(12) United States Patent
Wang et al.

(10) Patent No.: US 6,331,186 B1
(45) Date of Patent: Dec. 18, 2001

(54) END SLEEVE COATING FOR STENT DELIVERY

(75) Inventors: Lixiao Wang, Long Lake; The Thomas Trinh Tran, Coon Rapids; Fernando DiCaprio, Mendota Heights; Brett A. Williams, Lino Lakes, all of MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/427,805

(22) Filed: Oct. 27, 1999

Related U.S. Application Data

(63) Continuation-in-part of application No. 09/273,520, filed on Mar. 22, 1999.

(51) Int. Cl.⁷ .............................. A61F 2/02; A61M 25/10
(52) U.S. Cl. .......................................................... 623/1.11
(58) Field of Search ................................. 623/1.11, 1.17, 623/1.12, 1.23; 606/190, 194, 198

(56) References Cited

U.S. PATENT DOCUMENTS

| | | | |
|---|---|---|---|
| 4,950,227 | * 8/1990 | Savin et al. | 623/1.12 |
| 5,108,416 | 4/1992 | Ryan et al. . | |
| 5,160,790 | * 11/1992 | Elton | 428/412 |
| 5,295,978 | 3/1994 | Fan et al. | 604/265 |
| 5,403,341 | 4/1995 | Solar . | |
| 5,556,414 | * 9/1996 | Turi | 606/198 |
| 5,695,499 | * 12/1997 | Helgerson et al. | 606/108 |
| 5,800,517 | * 9/1998 | Anderson et al. | 623/1 |
| 5,843,158 | * 12/1998 | Lenker et al. | 623/1 |
| 5,944,726 | 8/1999 | Blaeser et al. | 608/108 |
| 6,010,521 | * 1/2000 | Lee et al. | 606/194 |
| 6,160,032 | * 12/2000 | Shah et al. | 523/112 |

* cited by examiner

*Primary Examiner*—Cary E. O'Connor
(74) *Attorney, Agent, or Firm*—Vidas, Arret & Steinkraus

(57) ABSTRACT

A stent delivery system which utilizes a stent delivery catheter to deliver a stent into a body lumen. The stent delivery catheter being equipped with at least one stent retaining sleeve. The at least one stent retaining sleeve having an inside diameter and an outside diameter. The inside diameter having a surface which is lubricious.

38 Claims, 3 Drawing Sheets

END SLEEVE COATING FOR STENT DELIVERY

RELATIONSHIP TO PRIOR APPLICATIONS

The present application is a continuation-in-part of U.S. application Ser. No. 09/273,520, filed Mar. 22, 1999 now U.S. Pat. No. 6,221,097.

BACKGROUND OF THE INVENTION

The patent relates to a delivery system in which a catheter carries on its distal end portion a stent which is held in place around the catheter prior to and during percutaneous delivery by means of one and preferably two end sleeves which have been coated with a lubricious material. The lubricious material is added to the sleeve material subsequent to extrusion of the sleeve material but prior to a heat curing step. As a result of the heat curing the lubricious material attains a gel or jellied consistency. The stent may be self-expanding, such as a NITINOL shape memory stent, or it may be expandable by means of an expandable portion of the catheter, such as a balloon.

Stents and stent delivery systems are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under a contained sheath or sleeve(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

An example is the stent described in PCT Application No. 960 3092 A1, published Feb. 8, 1996, the content of which is incorporated herein by reference.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly any potentially sharp or jagged edges of its distal and proximal ends, must be protected to prevent edge dissection and prevent abrasion and/or reduce trauma of the vessel walls.

Inflation expandable stent delivery and deployment systems are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all of these patents is incorporated herein by reference.

This invention provides an improvement over the cited art, by selectively coating or otherwise lubricating the sleeve subsequent to its extrusion yet prior to heat curing. This is in contrast to prior methods of lubricating the sleeve, such as by incorporating a lubricant additive within the polymeric composition of the sleeve, such as described in U.S. patent application Ser. No. 09/273,520, the entire contents of which is hereby incorporated by reference. In addition, the present invention avoids the use of collars, rings or other devices used to secure the sleeves to the catheter by bonding an end of a sleeve to the catheter directly.

BRIEF SUMMARY OF THE INVENTION

In the present invention, the sleeves are positioned around the catheter with one end portion of each sleeve connected thereto. The other end of each sleeve overlaps an opposite end portion of the stent to hold it in place on the catheter in a contracted condition. The sleeves are elastomeric in nature so as to stretch and release the stent when it is expanded for delivery. A viscous jelly-like lubricant material is provided on the inside surface of the sleeve between the sleeve and the balloon on the catheter. The viscous jelly-like lubricant material may also be provided on the outside surface of the sleeve. In a preferred embodiment, a fluid or dry lubricant is coated onto the sleeve material after it has been extruded. Examples of such lubricants include parylene and DICRO-NITE® (modified tungsten disulfide). Once the lubricant is applied the coated material is cured. The curing process leads to a gelling of the lubricant resulting in the presently desired lubricious yet viscous lubricant material which offers resistance to flow, herein termed a "lubricious gel" coating. Optionally, the lubricious gel coating may be followed by a dry lubricant.

The preferred embodiment of the lubricious gel, as described herein, is preferably characterized as being a silicone based lubricant which does not wick or migrate away from the sleeves. In alternative embodiments of the invention the outside diameters of the respective sleeves may be coated, or only specific portions of the sleeves are coated.

Non-crosslinkable hydrophilic lubricants which may be used with the present invention include: polyalkylene glycols; alkoxy polyalkylene; copolymers of methyl vinyl ether and maleic acid; pyrrolidones including poly (vinylpyrrolidone); acryl amides including poly(N-alkylacrylamide); poly(acrylic acid); poly(vinyl alcohol); poly(ethyleneimine); poly amides; methyl cellulose; hepartin; dextran; modified dextran; chondroitin sulfate; lecithin, etc. These polymers typically contain a hydrophilic group such as: $-OH$, $-CONH_2$, $-COOH$, $-NH_2$, $-COO-$, $-SO_3$, $-NR_3^+$, etc.

Some examples of crosslinkable hydrophilic lubricants which may alternatively be utilized with the present invention include: esterified polymers, salts, amides, anhydrides, halides, ethers, hydrolyzates, acetals, formals, alkylols, quaternary polymers, diazos, hydrazides, sulfonates, nitrates and ion complexes.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
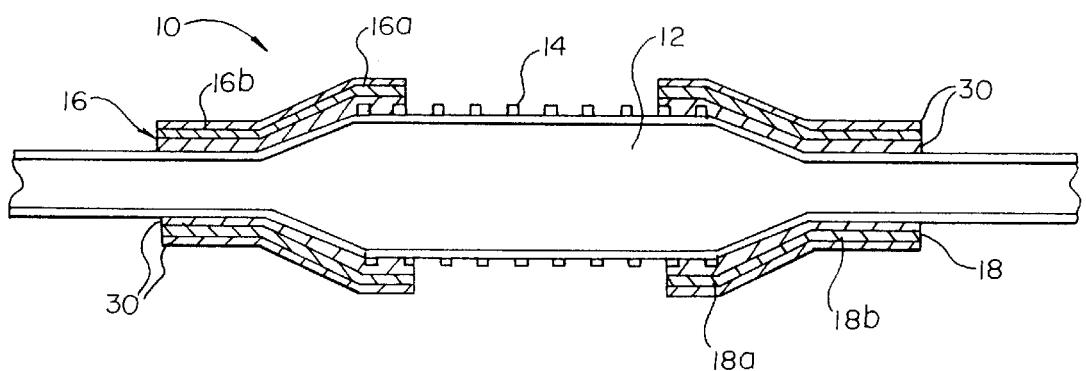
FIG. 1 is a schematic sectional side view of an embodiment of the inventive stent delivery system wherein the sleeves are coated with lubricious gel on their inside and outside diameters.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows an embodiment of the present invention wherein a catheter generally designated 10 has an expandable portion or balloon 12. The expandable portion may be an inherent part of the catheter, as shown, or alternatively may be a separate balloon which is affixed to the catheter in any of the manners which may be known to one of ordinary skill in the art. Disposed about balloon 12 is a stent 14 as shown. Stent 14 may be any stent type capable of being delivered by a stent delivery catheter, such stents may be self-expanding or balloon expandable.

Attached to the catheter 10 are a pair of sleeves 16, 18. The sleeves each include a first portion 16a, 18a. When the balloon 12 is in the non-inflated state first sleeve portions 16a, 18a overlay the ends of balloon 12 as well as the ends of stent 14 as shown. Sleeves 16 and 18 also include respective second portions 16b and 18b. Regardless of the state of the balloon 12, non-inflated or inflated, second sleeve portions 16b, 18b are fixedly attached to catheter 10. The second sleeve portions may be attached to the catheter utilizing any method of attachment known. Such methods of attachment may include, but are not limited to: bonding or welding the sleeves to the catheter surface, applying an adhesive between the catheter and sleeve surface, or employing a mechanical attachment device such as a retaining ring or collar as is well known in the art. Preferably, the sleeves each have a thickness within the range of 0.0010 to 0.0060 inches.

It is known in the art that in many stent delivery systems a silicone based lubricant is applied to stent retaining sleeves or socks after the delivery system is constructed and the sleeves are in place. However, it is also known that liquid silicone based lubricants applied in this manner tend to be drawn to or wick over the various surfaces of the stent. This is undesirable as the silicone based lubricant may then be introduced into the vessel wall of the patient when the stent is delivered into a body lumen, resulting in potential inflammation and restenosis. In addition, because the stent tends to wick the silicone based lubricant on both its upper and lower surfaces, the stent itself has reduced contact with the balloon surface. As a result it is more difficult to secure the stent to the balloon. The affected stent causes increased crimping pressure which results in crimping processes which may be prone to more readily cause the stent to rupture the balloon.

In this embodiment the present invention avoids the problems mentioned above, by placing a coating of lubricious gel 30 on the interior and exterior surfaces of sleeves 16 and 18 after the sleeve material has been extruded. In order to achieve the desired gel consistency, a suitable fluid lubricant is added to the sleeve material and then heat cured. Heat curing the fluid lubricant coating allows the coating to gel as is desired. The resulting lubricous coating has a gel-like state as defined herein above, and does not wick or have a tendency to migrate off of the sleeve as prior liquid silicone based lubricant coatings does.

For illustrative purposes, lubricious coating 30 is shown in the various drawings with a highly exaggerated thickness. When applied after extrusion, lubricious coating 30 is preferably a thin layer of silicone or a silicone based lubricant such as a mixture of 98% heptane and 2% silicone; a mixture of 2% Dow Corning MDX4-4159 and DC 360 silicone mixed with 98% heptane; sesame oil; silane or silane oligomers for example: amino-functional polydimethyl siloxane, sold under the tradename of SILASTIC® MDX4-4210, MDX4-4159; 1-methoxy-3-(trimethylsiloxy) butadiene; methyltrimethoxysilane; 1.1.3.3-tetramethyl-1.3-diethoxydisioxane; triethylacetoxysilane; triphenylsilanol, etc.

After the heat curing process is complete, preferably, the gelled lubricious coating 30 is a layer less than 0.0001 inches in thickness. The physical characteristics of the gelled lubricious coating are such that migration of the coating onto the surfaces of the stent is prevented, unlike the prior slip coatings described above. By preventing the coating from moving on to the stent, the present stent deployment system has reduced parameters for crimping the stent to the balloon, which provides for a crimping process which is much more balloon friendly.

Figure 2:
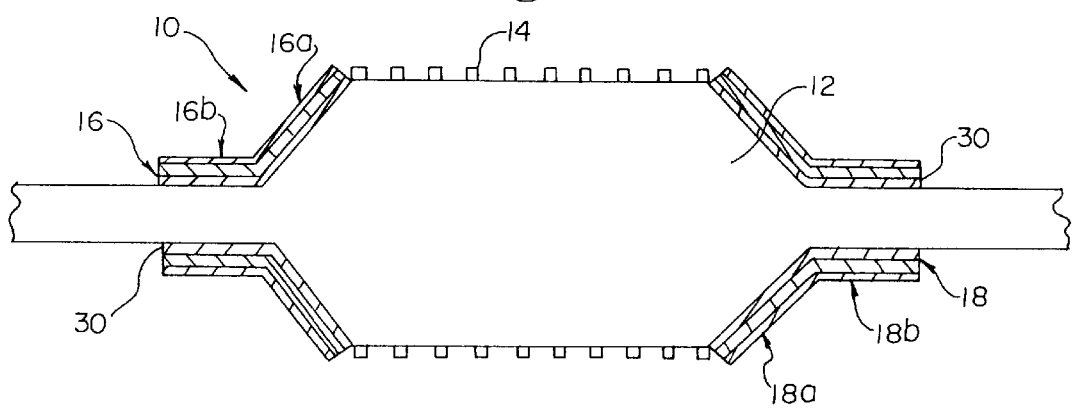
FIG. 2 is a similar view showing the embodiment of the stent delivery system shown in FIG. 1 when the balloon has been inflated to the inflated state.

Lubricious coating 30 assists in deployment of stent 14 by allowing the ends of balloon 12 and stent 14 to slide more readily away from the sleeves when balloon 12 is inflated, as seen in FIG. 2. Once the ends of stent 14 are no longer overlaid by sleeves 16 and 18 the stent is allowed to fully expand.

In one preferred embodiment of the present invention, as shown in FIG. 1, sleeves 16 and 18 may have a lubricious coating on both their inside diameter surfaces as well as their outside diameter surfaces. A lubricious coating on the outside diameter surfaces may provide improved trackability and movement of the catheter in a body lumen. In an alternative embodiment of the invention it may be desirable to include a sheath around the region of the catheter where the stent is mounted. A lubricious coating on the outside diameter surface of the sleeves may assist in the retraction of such a catheter sheath by reducing the amount of resistance the sheath must overcome in order to be retracted from the stent mounting region. In addition the outside lubricious coating, may reduce the likelihood of the sheath hooking or pulling on the sleeves or stent as it is pulled back.

Figure 3:
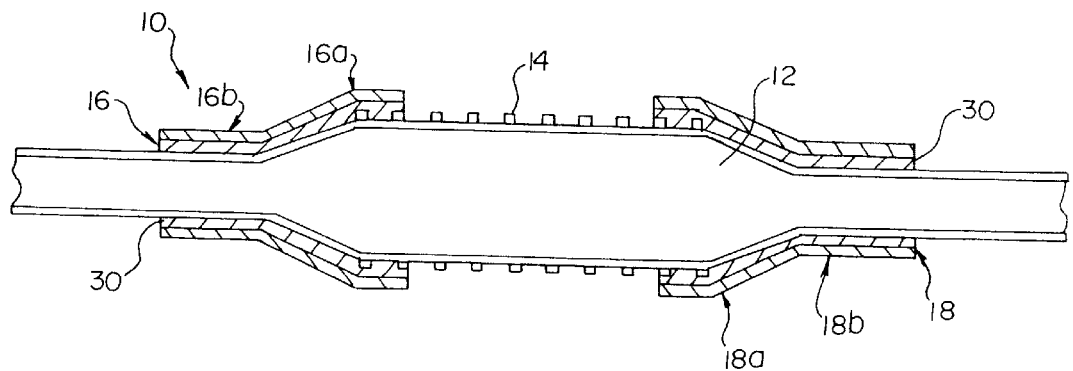
FIG. 3 is a similar view showing an embodiment of the stent delivery system wherein the sleeves are coated with lubricious gel on only their inside diameters.

In a further preferred embodiment of the present invention it may be desirable to coat only the inside diameter surfaces of the sleeves. As shown in FIG. 3, only the inside diameter surface of sleeves 16 and 18 are coated with lubricious coating 30.

Figure 4:
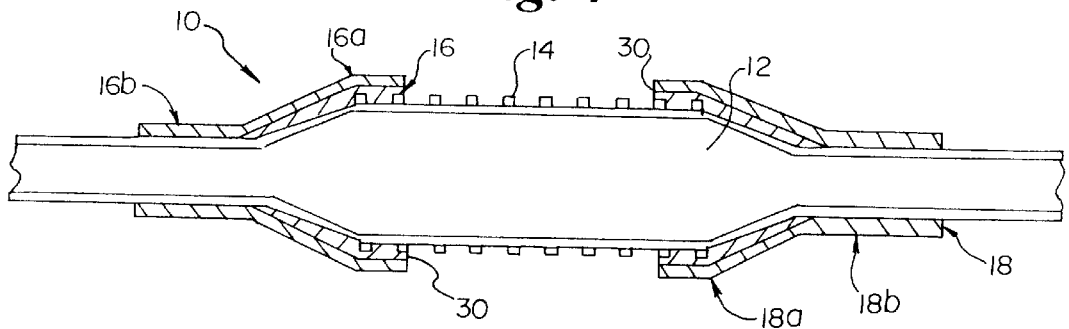
FIG. 4 is a similar view showing an embodiment of the stent delivery system wherein only a portion of the inside diameter of the sleeves is coated with lubricious gel.

Because different lubricious coating types may have diverse characteristics, some lubricious coatings may interfere with the attachment of the sleeves to the catheter. In such an instance, it may be desirable or necessary to coat only specific portions of the sleeves. More specifically, in order to ensure proper securement of second sleeve portions 16b and 18b to catheter 10 it may be desirable or necessary to avoid coating the second sleeve portions, as shown in FIG. 4. However, the benefits provided by lubricious coating 30 are substantially maintained in this instance by coating only the inside diameter surface of first sleeve portions 16a and 16b, thereby ensuring that the ends of the stent and balloon may be readily withdrawn from under the sleeves when the balloon is inflated.

Figure 5:
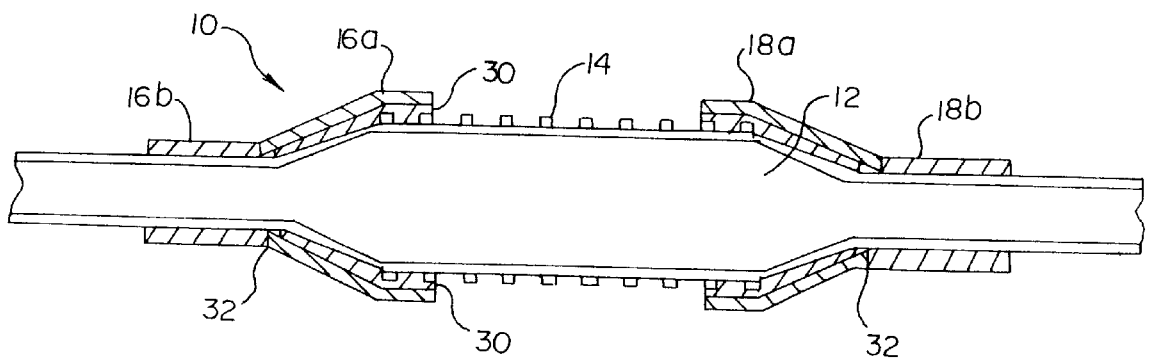
FIG. 5 is a similar view showing an embodiment of the stent delivery system wherein the sleeves are extruded from different polymer compositions which have then been bonded together.

Because of various manufacturing limitations inherent in the production of elastomeric polymer sleeves of the type described and preferably used herein, it is often more desirable to extrude and shape the polymer material into a tube which is to be used in the manufacture of the sleeve, then to separate the portion of the tube which will overlie the ends of the stent and balloon and separately coat these sections i.e., 16a and 18a. After the appropriate sections are coated they may be heat cured and then bonded, welded or otherwise attached to the uncoated sections 16b and 18b which will be connected to the catheter. The embodiment shown in FIG. 5 shows such the stent delivery system with such bonded sleeves. First sleeve sections 16a and 18a have lubricous coating 30 applied to their inside diameter surfaces. They are then connected to the second sleeve sections 16b, 18b with a weld 32. Weld 32 may be a lap weld, a butt weld, an adhesive or any other means of connection which may be known to one of ordinary skill in the art.

Figure 6:
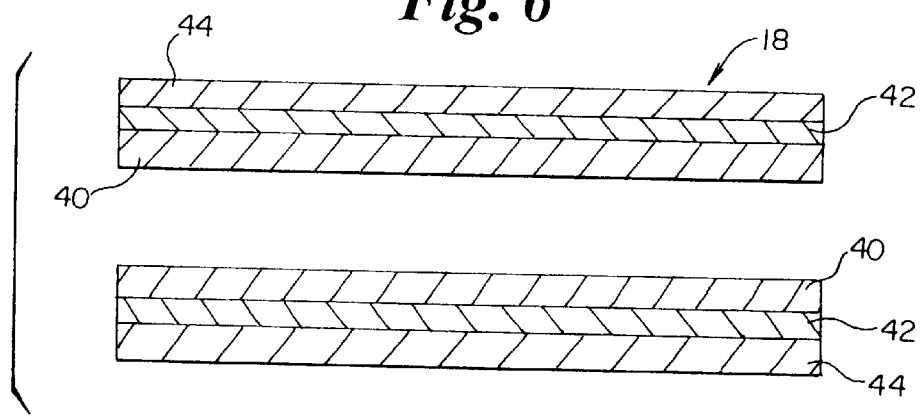
FIG. 6 is a similar view showing an embodiment of a stent delivery sleeve having a continuous tri-layer construction.
Figure 7:
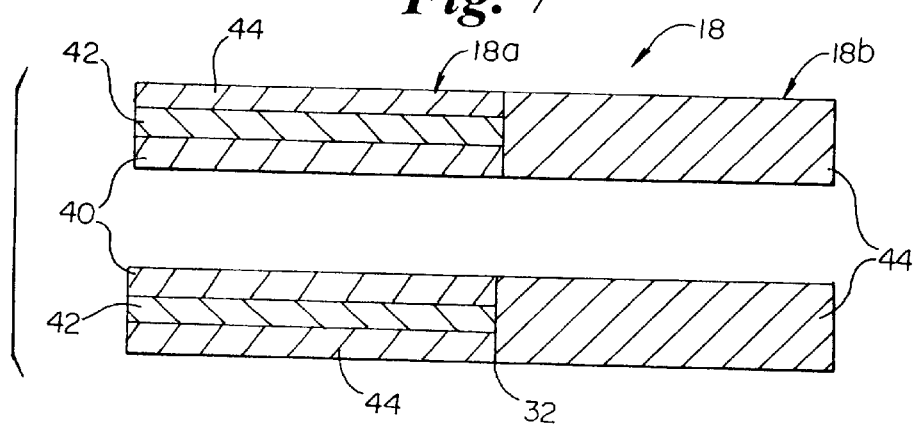
FIG. 7 is a similar view showing an embodiment of a stent delivery sleeve having a partial tri-layer construction.

Because stent retaining sleeves may be composed from materials which may be unsuitable for placing an effective layer of lubricious material upon, in another embodiment of the present invention the sleeves may have a tri-layer construction such as shown in FIGS. 6 and 7. Where the sleeves have a tri-layer construction the sleeves may be comprised of an inner layer 40 which is an inherently lubricous polymer such as polytetrafluoroethylene (PTFE), high density polyethylene (HDPE), acetal resins such as those available from the Dupont corporation such as DELTRIN® or other suitable polymer types.

In FIGS. 6 and 7, in order to show two potential embodiments of sleeves which may include the tri-layer construction described above, the sleeves are shown in an exaggerated scale. Furthermore, respective FIGS. 6 and 7 each show only a single sleeve 18, sleeve 16 is a left-handed mirror image of sleeve 18 as shown. In the embodiment shown in FIG. 6, inner layer 40 may extend through out the length of a sleeve 18 or in an alternative embodiment shown in FIG. 7, may be confined to only a portion of the sleeve such as the first sleeve portions 16a and 18a. Opposite the inner layer 40 is outer layer 44. Outer layer 44 is composed of any polymer material which can be used in any of the embodiments of the present invention already described herein, preferably having elastomer properties as well as heat shrinkable properties. The lubricious inner layer 40 and the outer polymer layer 44 are joined by an intermediate layer 42. The intermediate layer or third is composed of material which is characterized as being capable of bonding to the inner lubricous polymer material on one surface, and the outer sleeve polymer material on the other. Preferably, the intermediate layer is composed of PLEXAR® 380, thermoplastic polymers including polypropylene, polyurethane or other similar materials.

In the embodiment shown in FIGS. 7, it may also be more desirable to bond first sleeve portion 18a, to the second sleeve portion 18b, with a weld 32 or other method of attachment as described as described in relation to FIG. 5 above.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent delivery system comprising: a stent delivery catheter having an expandable portion and being equipped with at least one stent retaining sleeve, the at least one stent retaining sleeve being further characterized as having an inside diameter and an outside diameter, the inside diameter being at least partially coated with a lubricious gel which is a heat curing silicone based compound, a noncrosslinkable lubricant having at least one hydrophilic group, or a crosslinkable lubricant selected from esterified polymers, salts, amides, anhydrides, halides, ethers, hydrolyzates, acetals, formals, alkylols, quaternary polymers, diazos, hydrazides, sulfonates, nitrates, ion complexes, and mixtures thereof.

2. The stent delivery system of claim 1 wherein the at least one stent retaining sleeve is formed of material which is first extruded and then cured, the material being at least partially coated with a lubricious substance after the material is extruded but before the material is heat cured.

3. The stent delivery system of claim 2 the at least one stent retaining sleeve further comprising a coating of dry lubricant material.

4. The stent delivery system of claim 1 wherein the outside diameter is at least partially coated with lubricious gel.

5. The stent delivery system of claim 1 wherein the lubricious gel includes a silicone.

6. The stent delivery system of claim 1 wherein the lubricious gel includes a non-silicone based lubricant.

7. The stent delivery system of claim 1 wherein the inside diameter is further characterized as having a first portion and a second portion, the first portion being the portion of the inside diameter which overlays the stent on the expandable portion of the catheter, the second portion being the portion of the inside diameter which is attached to the catheter, at least the first portion being coated with a lubricious gel.

8. The stent delivery catheter of claim 1 wherein the at least one sleeve is an extruded polymer.

9. The stent delivery system of claim 1 wherein the at least one sleeve is further characterized as having a first portion and a second portion, the first portion being the portion of the at least one sleeve which overlays the stent on the expandable portion of the catheter, the second portion being the portion of the at least one sleeve which is attached to the catheter, the first portion being composed of an extruded polymer in combination with the lubricious gel, there being no lubricious gel in the composition of the second portion.

10. The stent delivery system of claim 9 wherein the first portion and the second portion are bonded together.

11. The stent delivery system of claim 10 wherein the first portion and the second portion are laser bonded together.

12. The stent delivery system of claim 9 wherein the first portion and the second portion are welded together.

13. The stent delivery system of claim 1 wherein said lubricious gel comprises a polydimethylsiloxane.

14. The stent delivery system of claim 1 wherein said lubricious gel further comprises at least one non-crosslinkable silicone.

15. The stent delivery system of claim 1 wherein said lubricious gel comprises a blend of a non-crosslinkable polydimethylsiloxane and a crosslinkable amino-terminated polydimethylsiloxane.

16. A stent delivery system comprising:

a catheter;

a medical balloon mounted on the catheter, the medical balloon having a non-inflated state and being inflatable to an inflated state, the medical balloon characterized as including:

a proximal end, a body portion, and a distal end;

a stent disposed about at least the body portion of the medical balloon, the stent having a first end and a second end, and a pair of stent retaining sleeves, the stent retaining sleeves having an inside diameter and an outside diameter, at least a portion of the inside diameter of the sleeves being coated with a lubricious gel which is a heat curing silicone based compound, a noncrosslinkable lubricant having at least one hydrophilic group, or a crosslinkable lubricant selected from esterified polymers, salts, amides, anhydrides, halides, ethers, hydrolyzates, acetals, formals, alkylols, quaternary polymers, diazos, hydrazides, sulfonates, nitrates, ion complexes, and mixtures thereof, the sleeves being further characterized as a proximal sleeve and a distal sleeve, each sleeve having a balloon engagement end and a catheter attachment end, the balloon engagement end of the proximal sleeve overlying the proximal end of the medical balloon and the balloon engagement end of the distal sleeve overlying the distal end of the medical balloon when the balloon is in either the non-inflated or inflated states, the balloon engagement end of the proximal sleeve overlying the first end of the stent on the medical balloon when the medical balloon is in the non-inflated state and the balloon engagement end of the distal sleeve overlying the second end of the stent on the medical balloon when the medical balloon is in the non-inflated state, the balloon engagement end of the proximal sleeve and the balloon engagement end of the distal sleeve being withdrawn from the stent when the medical balloon is in the inflated state, the catheter attachment ends of the sleeves being attached to the catheter.

17. The stent delivery system of claim 16 wherein the inside diameter of the balloon engagement end of each sleeve is coated with a lubricious gel.

18. A stent delivery system comprising: a stent delivery catheter which is equipped with at least one stent retaining sleeve, the at least one stent retaining sleeve having an inside layer and an outside layer, at least a portion of the inside layer having a surface which is coated with a lubricous gel.

19. The stent delivery system of claim 18 wherein the at least a portion of the inside layer is at least partially composed of a lubricious gel.

20. The stent delivery system of claim 18 further including an intermediate layer, the intermediate layer having a first surface and a second surface, the first surface attached to the at least a portion of the inside layer having a surface which is lubricious, the second surface attached to the outside layer.

21. The stent delivery catheter of claim 20 wherein the intermediate layer is composed of anhydride modified linear low density polyethylene.

22. The stent delivery system of claim 18 wherein said lubricious gel comprises a polydimethylsiloxane.

23. The stent delivery system of claim 18 wherein said lubricious gel further comprises at least one non-crosslinkable silicone.

24. The stent delivery system of claim 18 wherein said lubricious gel comprises a blend of a non-crosslinkable polydimethylsiloxane and a crosslinkable amino-terminated polydimethylsiloxane.

25. A stent delivery system having a stent delivery catheter, the stent delivery catheter having an inflatable portion and a stent disposed thereabout, the stent delivery catheter being further equipped with a pair of stent retaining sleeves, the stent retaining sleeves each comprising:

a stent retaining portion, the stent retaining portion overlying at least an end of the stent as well as an end of the inflatable portion when the inflatable portion is in a non-inflated state, the stent retaining portion having a surface which includes a lubricious gel which is a heat curing silicone based compound, a noncrosslinkable lubricant having at least one hydrophilic group, or a crosslinkable lubricant selected from esterified polymers, salts, amides, anhydrides, halides, ethers, hydrolyzates, acetals, formals, alkylols, quaternary polymers, diazos, hydrazides, sulfonates, nitrates, ion complexes, and mixtures thereof;

a catheter attachment portion, the catheter attachment portion being attached to the catheter.

26. The stent delivery system of claim 25 wherein the lubricious gel is a coating.

27. The stent delivery system of claim 25 wherein the catheter attachment portion is attached to the catheter by a chemical bond.

28. The stent delivery system of claim 25 wherein stent retaining portion and the catheter attachment portion are attached with a weld.

29. The stent delivery system of claim 25 wherein the stent retaining portion has an inner layer and an outer layer, the inner layer characterized as being lubricious.

30. The stent delivery system of claim 29 further comprising an intermediate layer, the intermediate layer having a first surface attached to the inner layer and a second surface attached to the outer layer.

31. The stent delivery system of claim 30 wherein the catheter attachment portion is attached to the catheter by a weld.

32. The stent delivery system of claim 31 wherein the weld is a thermal, chemical or laser weld.

33. A method of manufacturing a tube which is suitable for constructing stent retaining sleeves comprising the steps of:

a) extruding the tube material;

b) applying a coating of lubricious material which is a heat curing silicone based compound, a noncrosslinkable lubricant having at least one hydrophilic group, or a crosslinkable lubricant selected from esterified polymers, salts, amides, anhydrides, halides, ethers, hydrolyzates, acetals, formals, alkylols, quaternary polymers, diazos, hydrazides, sulfonates, nitrates, ion complexes, and mixtures thereof to the tube material; and c) heat curing the tube, the heat curing causing the lubricious material to gel.

34. The method of manufacturing a tube which is suitable for constructing stent retaining sleeves of claim 33 further comprising the step of:

applying a layer of dry lubricant over the lubricious material after the tube has been heat cured.

35. The method of manufacturing a tube of claim 34 wherein the dry lubricant is parylene or modified tungsten disulfide.

36. A method of manufacturing a tube which is suitable for constructing stent retaining sleeves comprising the steps of:

(a) extruding sleeve material; and (b) applying a dry lubricant to the sleeve material.

37. The method of manufacturing a tube of claim 36 wherein the dry lubricant is parylene or modified tungsten disulfide.

38. The method of claim 36 further comprising the step of applying a lubricious gel coating prior to applying said dry lubricant to said sleeve material.

* * * * *